(12) United States Patent
Pietrzynski et al.

(10) Patent No.: US 8,912,215 B2
(45) Date of Patent: *Dec. 16, 2014

(54) RAPAMYCIN COMPOSITION

(75) Inventors: Grzegorz Pietrzynski, Montreal (CA); Valery Alakhov, Ile Bizard (CA); Kishore Patel, Pierrefonds (CA)

(73) Assignee: Everon Biosciences, Inc., Buffalo, NY (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/324,407

(22) Filed: Dec. 13, 2011

(65) Prior Publication Data

US 2013/0150397 A1   Jun. 13, 2013

(51) Int. Cl.
*A61K 31/436* (2006.01)

(52) U.S. Cl.
CPC .................. *A61K 31/436* (2013.01)
USPC .......................................... 514/291

(58) Field of Classification Search
None
See application file for complete search history.

(56) References Cited

U.S. PATENT DOCUMENTS

| | | | |
|---|---|---|---|
| 5,387,589 A | 2/1995 | Kulkarni | |
| 5,840,319 A | 11/1998 | Alakhov et al. | |
| 6,060,518 A | 5/2000 | Kabanov et al. | |
| 6,387,406 B1 | 5/2002 | Kabanov et al. | |
| 7,083,802 B2 | 8/2006 | Peyman | |
| 8,163,726 B2 | 4/2012 | Wen et al. | |
| 8,222,271 B2 | 7/2012 | Kleinman et al. | |
| 8,257,725 B2 | 9/2012 | Cromack et al. | |
| 2003/0054042 A1* | 3/2003 | Liversidge et al. | 424/489 |
| 2003/0118550 A1 | 6/2003 | Kabanov et al. | |
| 2004/0006012 A1* | 1/2004 | Cottens et al. | 514/11 |
| 2005/0064010 A1 | 3/2005 | Cooper et al. | |
| 2006/0247265 A1 | 11/2006 | Clackson et al. | |
| 2007/0059336 A1 | 3/2007 | Hughes et al. | |
| 2007/0196493 A1* | 8/2007 | Klinski et al. | 424/486 |
| 2007/0203173 A1 | 8/2007 | Mudumba et al. | |
| 2008/0268051 A1 | 10/2008 | Hughes et al. | |
| 2008/0275076 A1 | 11/2008 | Holm et al. | |
| 2008/0318843 A1 | 12/2008 | Schultz et al. | |
| 2009/0035381 A1 | 2/2009 | Stankus et al. | |
| 2009/0053391 A1 | 2/2009 | Ludwig et al. | |
| 2009/0074786 A1 | 3/2009 | Dor et al. | |
| 2009/0074859 A1 | 3/2009 | Patel | |
| 2009/0092665 A1 | 4/2009 | Mitra et al. | |
| 2009/0291073 A1 | 11/2009 | Ward et al. | |
| 2010/0040669 A1 | 2/2010 | Higuchi | |
| 2011/0033538 A1 | 2/2011 | Karavas et al. | |
| 2011/0110932 A1 | 5/2011 | Patel | |
| 2011/0142914 A1 | 6/2011 | Persaud et al. | |
| 2012/0114637 A1 | 5/2012 | Nivaggioli et al. | |

FOREIGN PATENT DOCUMENTS

| | | | |
|---|---|---|---|
| WO | 2004027027 A2 | 4/2004 | |
| WO | 2006102378 A2 | 9/2006 | |
| WO | 2008022256 A2 | 2/2008 | |
| WO | 2008078095 A1 | 7/2008 | |
| WO | 2008134644 A1 | 11/2008 | |
| WO | 2009005673 A1 | 1/2009 | |
| WO | 2009023877 A2 | 2/2009 | |

OTHER PUBLICATIONS

"Solubilization of rapamycin" by Simamora et al., Int. J. Pharmaceut. 213, 25-29 (2001).*
"Enhancing the bioavailability of ABT-963 using solid dispersion containing Pluronic F-68" by Chen et al., Int. J. Pharmaceut. 286, 69-80 (2004).*
"A new self-emulsifying formulation of itraconazole with improved dissolution and oral absorption" by Hong et al., J. Control. Release 110, 332-38 (2006).*
"Pharmacokinetics, tissue distribution and bioavailability of clozapine solid lipid nanoparticles after intravenous and intraduodenal administration" by Manjunath et al., J. Control. Release 107, 215-28 (2005).*
"The effects of mixed MPEG-PLA/Pluronic copolymer micelles on the bioavailability and multidrug resistance of docetaxel" by Mu et al., Biomaterials 31, 2371-79 (2010).*
Machado et al., Solid-liquid equilibrium of alpha-lactose in ehtanol/water, Fluid Phase Equilibria 173 (2000) pp. 121-134.
Batrakova et al., Anthracycline antibiotics non-covalently incorporated into the block copolymer micells: in vivo evaluation of anti-cancer activity, British Journal of Cancer (1996) 74, pp. 1545-1552.
Alakhov et al., Hypersensitization of Multidrug Resistant Human Ovarian Carcinoma Cells by Pluronic P85 Block Copolymer, Bioconjugate Chem. (1996), 7, pp. 209-216.
Ezdinli et al., Chemotherapy of Advanced Esophageal Carcinoma: Eastern Cooperative Oncology Group Experience, Cancer 46:2149-2153 (1980).
Valle et al., A phase 2 study of SP1049C, doxorubicin in P-glycoprotein-targeting pluronics, in patients with advanced adenocarcinoma of the esophagus and gastroesophageal junction, Invest. New Drugs, Feb. 24, 2010 pp. 1-9.

* cited by examiner

*Primary Examiner* — Theodore R West
(74) *Attorney, Agent, or Firm* — Hodgson Russ LLP

(57) ABSTRACT

In one aspect, the present invention is directed to a dry, flowable and compressible rapamycin composition comprising a specific mixture of hydrophobic and hydrophilic poly(ethylene oxide)-polypropylene oxide)-poly(ethylene oxide) block copolymers. In other aspects, the present invention is directed to a method of making the composition.

17 Claims, No Drawings

RAPAMYCIN COMPOSITION

FIELD OF THE INVENTION

In one aspect, the present invention is directed to a dry, flowable and compressible rapamycin composition comprising rapamycin and a mixture of hydrophobic and hydrophilic poly(ethylene oxide)-poly(propylene oxide)-poly(ethylene oxide) block copolymers. In other aspects, the present invention is directed to a method of making the composition.

THE NAMES OF THE PARTIES TO A JOINT RESEARCH AGREEMENT

This invention is the result of a joint research agreement between Tartis, Inc., parent company of Tartis-Aging, and Supratek Pharma Inc.

BACKGROUND OF THE INVENTION

Rapamycin, or sirolimus, is a macrolide which was first discovered as a product of the bacterium *Streptomyces hygroscopicus* in a soil sample from Easter Island. Although marketed primarily as an immunosuppressant, more recently several additional indications have been reported for this drug. In several of these indications, it would be useful to increase the amount of rapamycin which could be retained in certain cell types.

The use of certain poly(ethylene oxide)-poly(propylene oxide)-poly(ethylene oxide) block copolymers having a hydrophobe content of 50% or more by weight as pharmaceutical excipients to enhance the uptake of active materials in certain cell types has been described in a number of publications. See, for example, U.S. Pat. No. 5,840,319; U.S. Pat. No. 6,060,518; Alakhov et al., "*Hypersensitization of Multidrug Resistant Human Ovarian Carcinoma Cells by Pluronic P85 Block Coploymer*", Bioconjugate Chem. 7, 209-216 (1996); and Batrakova et al., "*Anthracycline antibiotics non-covalently incorporated into copolymer micelles: in vivo evaluation of anti-cancer activity*"; British Journal of Cancer 74: 1545-1552 (1996). It is believed that this effect is achieved by the inhibition of ABC mediated efflux mechanisms in such cells. See U.S. Pat. No. 6,387,406.

Unfortunately, such hydrophobic block copolymers (also know an poloxamers; sold under the trade name Pluronics) have been found to aggregate in aqueous solutions at physiological temperatures (see U.S. Pat. No. 6,387,406, Example 34). Such aggregation under physiological conditions can be eliminated by blending such hydrophobic poloxamers with certain hydrophilic poloxamers as described in U.S. Pat. No. 6,387,406.

The use of such mixtures of hydrophilic and hydrophobic copolymers has been shown to greatly increase the effectiveness of certain drugs in clinical studies. Thus, Valle et al.; "*A phase 2 study of SP1049C, doxorubicin in P-gylcoprotein-targeting plurorics, in patients with advanced adenocarcinoma of the esophagus and gastroesophageal junction*"; Invest New Drugs; DOI 10.1007/s10637-010-9399-1; published 24 Feb. 2010, describes a Phase II study in which SP 1049C (a composition comprising doxorubicin, hydrophobic Pluronic L61 and hydrophilic Pluronic F127) displayed a response rate of 47% in the evaluable patient population (43% in the ITT formulation). In contrast, Ezdinli et al. "*Chemotherapy of Advanced Esophageal Carcinoma*"; Cancer 46:2149-2153; 1980; indicates that Adriamycin (a free doxorubicin formulation) elicited a response rate of only 5% when evaluated as a monotherapy in a Phase II study on patients with advanced esophageal cancer (see first full paragraph on page 2152, first column).

Unfortunately, the formulation of hydrophobic and hydrophilic block copolymers employed in the Valle study prepared by mixing Pluronic L61 with Pluronic F127 in an aqueous solution (along with the active material), and freeze drying the mixture to form a waxy pellet does not rapidly dissolve in aqueous solutions. See U.S. Patent Application Publication No. 2007/0196493. Accordingly, such composition requires caution if used in a typical hospital situation, as time must be taken to ensure that the waxy polymeric mixture has fully dissolved in the liquid application medium (typically saline) before administration to patients. U.S. Patent Application Publication No. 2007/0196493 discloses that such waxy mixture will rapidly dissolve in aqueous media if a sugar or similar material, preferably lactose, is incorporated into the polymer matrix by including such material in the aqueous solution which is dried to form the polymeric composition.

While U.S. Patent Application Publication No. 2007/0196493 discloses a mixture which will rapidly dissolve in aqueous media, the waxy nature of such composition makes it unsuitable for use in pills or other similar forms of administration.

Therefore, there is a need for pharmaceutical formulations of rapamycin which can take advantage of the ABC mediated efflux inhibition exhibited by hydrophobic poloxamers (which copolymers are liquids at room temperature), which formulations do not aggregate under physiological conditions, and which are suitable for the production of tablets and other dry forms of application.

Accordingly, it is an object of this invention to provide a rapamycin composition comprising such hydrophobic poloxamers, which composition is in the form of a free flowing, compressible powder.

It is a further object of this invention to provide a method of making the rapamycin composition.

SUMMARY OF THE INVENTION

In one aspect, the present invention is directed to a dry, flowable and compressible composition comprising:
 a. a hydrophobic poly(ethylene oxide)-polypropylene oxide)-poly(ethylene oxide) block copolymer;
 b. a hydrophilic poly(ethylene oxide)-polypropylene oxide)-poly(ethylene oxide) block copolymer; and
 c. Rapamycin.

In another aspect, this invention is directed to a process for making a dry, flowable and compressible rapamycin composition comprising the steps of
 a. mixing:
  i. a hydrophobic poly(ethylene oxide)-polypropylene oxide)-poly(ethylene oxide) block copolymer;
  ii. a hydrophilic poly(ethylene oxide)-polypropylene oxide)-poly(ethylene oxide) block copolymer; and
  iii. rapamycin;
 in an organic solvent to form an organic composition; and
 b. drying the organic composition.

DETAILED DESCRIPTION OF THE INVENTION

In one aspect, the present invention is directed to a dry, flowable and compressible composition comprising:
 a. a hydrophobic poly(ethylene oxide)-polypropylene oxide)-poly(ethylene oxide) block copolymer;
 b. a hydrophilic poly(ethylene oxide)-poly(propylene oxide)-poly(ethylene oxide) block copolymer; and
 c. rapamycin.

Preferably, the composition comprises rapamycin and a mixture selected from the group consisting of:

i. (a) a hydrophobic poly(ethylene oxide)-polypropylene oxide)-poly(ethylene oxide) block copolymer having an average molecular weight of about 2000 and a hydrophobe weight percentage of about 90% and (b) a hydrophilic poly(ethylene oxide)-polypropylene oxide)-poly(ethylene oxide) block copolymer having an average molecular weight of about 12,600 and a hydrophobe weight percentage of about 30%, having a w/w proportion of a:b of about 1:4 or higher;

ii. (a) a hydrophobic poly(ethylene oxide)-polypropylene oxide)-poly(ethylene oxide) block copolymer having an average molecular weight of about 2750 and a hydrophobe weight percentage of about 90% and (b) a hydrophilic poly(ethylene oxide)-polypropylene oxide)-poly(ethylene oxide) block copolymer having an average molecular weight of about 12,600 and a hydrophobe weight percentage of about 30%, having a w/w proportion of a:b of about 1:3 or higher;

iii. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 7,700 and a hydrophobe weight percentage of about 30%, having a w/w proportion of a:b of about 1:4 or higher;

iv. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 14,600 and a hydrophobe weight percentage of about 20%, having a w/w proportion of a:b of about 1:3 or higher; and v. (a) a hydrophobic poly(ethylene oxide)-poly(propylene oxide)-poly(ethylene oxide) block copolymer having an average molecular weight of about 3650 and a hydrophobe weight percentage of about 80% and (b) a hydrophilic poly(ethylene oxide)-poly(propylene oxide)-poly(ethylene oxide) block copolymer having an average molecular weight of about 12,600 and a hydrophobe weight percentage of about 30%, having a w/w proportion of a:b of about 1:4 or higher.

Most preferably, the composition comprises:

i. (a) a poly(ethylene oxide)-poly(propylene oxide)-poly(ethylene oxide) block copolymer having an average molecular weight of about 3650 and a hydrophobe weight percentage of about 80% and (b) a poly(ethylene oxide)-poly(propylene oxide)-poly(ethylene oxide) block copolymer having an average molecular weight of about 12,600 and a hydrophobe weight percentage of about 30%, having a w/w proportion of (a):(b) of about 1:4 or higher; and ii. rapamycin.

As is employed herein, the phrase "or higher", when employed in conjunction with a block copolymer ratio, is intended to mean that the second number in the ratio may be higher than the number presented. Thus, for example, the phrase "1:4 or higher" is intended to include 1:5, but is not intended to include 1:2.

As is employed herein, the term "rapamycin" is intended to include pharmaceutically acceptable salts of rapamycin.

In addition, as is employed herein, the term "about" when employed in conjunction with a value such as a molecular weight or weight percent composition is intended to mean the stated value and a range of values one having ordinary skill in the art would recognize as providing a composition having the properties of the present invention.

Further, as is employed herein, the term "hydrophobe weight percentage" is intended to mean the weight percentage of poly(propylene oxide) contained in the block copolymer. Thus, a "hydrophobic" block copolymer will contain a higher weight percentage of poly(propylene oxide) than poly (ethylene oxide); and a "hydrophilic" block copolymer will contain a higher weight percentage of poly(ethylene oxide) than polypropylene oxide).

The poly(ethylene oxide)-polypropylene oxide)-poly(ethylene oxide) block copolymers employed in the composition of the present invention are commercially available under the trademark Pluronic from BASF Corporation. Specifically, the following descriptions above apply to the following Pluronics:

Pluronic L61 A poly(ethylene oxide)-polypropylene oxide)-poly(ethylene oxide) block copolymer having an average molecular weight of 2000 and a hydrophobe weight percentage of 90%.

Pluronic L81 A poly(ethylene oxide)-polypropylene oxide)-poly(ethylene oxide) block copolymer having an average molecular weight of 2750 and a hydrophobe weight percentage of 90%.

Pluronic L92 A poly(ethylene oxide)-polypropylene oxide)-poly(ethylene oxide) block copolymer having an average molecular weight of 3650 and a hydrophobe weight percentage of 80%.

Pluronic F87 A poly(ethylene oxide)-polypropylene oxide)-poly(ethylene oxide) block copolymer having an average molecular weight of 7700 and a hydrophobe weight percentage of 30%.

Pluronic F108 A poly(ethylene oxide)-polypropylene oxide)-poly(ethylene oxide) block copolymer having an average molecular weight of 14,600 and a hydrophobe weight percentage of 20%.

Pluronic F127 A poly(ethylene oxide)-polypropylene oxide)-poly(ethylene oxide) block copolymer having an average molecular weight of 12,600 and a hydrophobe weight percentage of 30%.

Thus, the dry, flowable and compressible excipient compositions of the present invention can comprise the following mixtures:

i. Pluronic L61 with Pluronic F127, w/w proportion of about 1:4 or higher;

ii. Pluronic L81 with Pluronic F127, w/w proportion of about 1:3 or higher;

iii. Pluronic L92 with Pluronic F87, w/w proportion of about 1:4 or higher;

iv. Pluronic L92 with Pluronic F108, w/w proportion of about 1:3 or higher; or v. Pluronic L92 with Pluronic F127, w/w proportion of about 1:4 or higher; with rapamycin.

The composition can have a broad range of hydrophilic poloxamer to hydrophobic poloxamer ratios. In an embodiment, the composition comprises a ratio of hydrophilic poloxamer to hydrophobic poloxamer of from 1:3 to 1:25, including all integer values between 1:3 and 1:25 (e.g., 1:3, 1:4, 1:5, 1:6 and so on up to 1:25). A suitable excipient will comprise at least about 5% by weight of hydrophilic poloxamer (e.g., F127) based upon the total weight of hydrophobic plus hydrophilic poloxamer (a 1:19 w/w proportion); and generally will comprise at least about 10% by weight hydrophilic poloxamer (a 1:9 w/w proportion).

The compositions of the present invention can comprise a broad range of total poloxamer (hydrophobic poloxamer plus hydrophilic poloxamer) to rapamycin ratios. In general, such ratios will generally be between about 100:1 and about 1:1; are typically between about 75:1 and about 2:1; are preferably between about 60:1 and about 20:1; and are more preferably between about 50:1 and 40:1; all by weight.

The rapamycin compositions of the present invention are dry flowing compressible powders possessing Carr Indices of less than about 20, preferably of less than about 10, and most preferably of about 5 or less. Such flowability is unexpected, given that identical block copolymer mixtures produced employing water rather than an organic solvent exhibit much higher Carr Indices. Consequently, such compositions exhibit unexpectedly desirable compressibility.

Further, it is unexpected that such compositions are free flowing, given that the hydrophobic poloxamer employed is a liquid while the hydrophilic poloxamers employed are waxy solids.

The rapamycin compositions of this invention comprise a sufficient amount of active ingredient such that a therapeutical dosage can be provided to a patient, which amount can be readily determined by one of ordinary skill in the art. It will be understood that the precise dosage will vary with age, size, sex and condition of the subject as well as the severity of the disorder to be treated and the like and be subject to the physician's discretion.

In addition to the mixed poloxamer excipient and rapamycin, the pharmaceutical compositions of this invention can further contain other pharmaceutically acceptable excipients, such as sugars, polyalcohols, soluble polymers, salts and lipids. Suitable sugars and polyalcohols which can be employed include, without limitation, lactose, sucrose, mannitol, and sorbitol. Illustrative of the soluble polymers which can be employed are polyoxyethylene, poloxamers, polyvinylpyrrolidone, and dextran. Useful salts include, without limitation, sodium chloride, magnesium chloride, and calcium chloride. Lipids which can be employed include, without limitation, fatty acids esters, glycolipids, and phospholipids. Typically, such additional excipients will be blended with the dry polyoxamer/rapamycin composition.

Typically, the compositions of this invention will further comprise a stabilizer which prevents the decomposition of rapamycin in alkali environments. Any pharmaceutically acceptable pH modifier which keeps the formulation from becoming alkaline may be employed. Examples of such stabilizers include ascorbic acid, lactic acid and citric acid; with citric acid being particularly preferred.

The dry, flowable and compressible rapamycin compositions of this invention can be prepared by a process comprising the steps of:

a. mixing a (i) a hydrophobic poly(ethylene oxide)-polypropylene oxide)-poly(ethylene oxide) block copolymer; (ii) a hydrophilic poly(ethylene oxide)-poly(propylene oxide)-poly(ethylene oxide) block copolymer; and (iii) rapamycin in an organic solvent to form an organic mixture; and b. drying the organic mixture.

Preferably, the compositions are formed by:

(A) mixing rapamycin with a combination of poly(ethylene oxide)-polypropylene oxide)-poly(ethylene oxide) block copolymers selected from the group consisting of:

i. (a) a poly(ethylene oxide)-polypropylene oxide)-poly(ethylene oxide) block copolymer having an average molecular weight of about 2000 and a hydrophobe weight percentage of about 90% and (b) a poly(ethylene oxide)-polypropylene oxide)-poly(ethylene oxide) block copolymer having an average molecular weight of about 12,600 and a hydrophobe weight percentage of about 30%, having a w/w proportion of a:b of about 1:4 or higher;

ii. (a) a poly(ethylene oxide)-poly(propylene oxide)-poly(ethylene oxide) block copolymer having an average molecular weight of about 2750 and a hydrophobe weight percentage of about 90% and (b) a poly(ethylene oxide)-poly(propylene oxide)-poly(ethylene oxide) block copolymer having an average molecular weight of about 12,600 and a hydrophobe weight percentage of about 30%, having a w/w proportion of a:b of about 1:3 or higher;

iii. (a) a poly(ethylene oxide)-poly(propylene oxide)-poly(ethylene oxide) block copolymer having an average molecular weight of about 3650 and a hydrophobe weight percentage of about 80% and (b) a poly(ethylene oxide)-poly(propylene oxide)-poly(ethylene oxide) block copolymer having an average molecular weight of about 7,700 and a hydrophobe weight percentage of about 30%, having a w/w proportion of a:b of about 1:4 or higher;

iv. (a) a poly(ethylene oxide)-poly(propylene oxide)-poly(ethylene oxide) block copolymer having an average molecular weight of about 3650 and a hydrophobe weight percentage of about 80% and (b) a poly(ethylene oxide)-poly(propylene oxide)-poly(ethylene oxide) block copolymer having an average molecular weight of about 14,600 and a hydrophobe weight percentage of about 20%, having a w/w proportion of a:b of about 1:3 or higher; and v. (a) a poly(ethylene oxide)-poly(propylene oxide)-poly(ethylene oxide) block copolymer having an average molecular weight of about 3650 and a hydrophobe weight percentage of about 80% and (b) a poly(ethylene oxide)-poly(propylene oxide)-poly(ethylene oxide) block copolymer having an average molecular weight of about 12,600 and a hydrophobe weight percentage of about 30%, having a w/w proportion of a:b of about 1:4 or higher; in an organic solvent to form an organic mixtur; and (B) drying the organic mixture.

Most preferably, such compositions are prepared by:

a. mixing rapamycin with one or more members selected from the group consisting of mixtures of:

i. Pluronic L61 with Pluronic F127, w/w proportion of about 1:4 or higher;

ii. Pluronic L81 with Pluronic F127, w/w proportion of about 1:3 or higher;

iii. Pluronic L92 with Pluronic F87, w/w proportion of about 1:4 or higher;

iv. Pluronic L92 with Pluronic F108, w/w proportion of about 1:3 or higher; and v. Pluronic L92 with Pluronic F127, w/w proportion of about 1:4 or higher; with an organic solvent to form an organic composition; and b. drying the organic composition.

Preferred organic solvents which can be employed include alcohols, particularly ethanol, and halogenated hydrocarbons, particularly dichloromethane. The mixing is typically conducted at room temperature and pressure, although higher or lower temperatures and/or pressures may be employed.

In certain embodiments, it may be useful for a minor amount of water to be blended with the organic solvent. Typically, in such situations, the water will comprise less than about 25% by weight, preferably less than about 10% by weight of the water/organic solvent mixture.

Any conventional method of drying can be utilized. The preferred methods of drying are drying in vacuum and spray drying. In utilizing these methods any of the conventional techniques for carrying them out may be employed.

In certain embodiments, the rapamycin can be incorporated into the mixed poloxamer excipient by adding it to the poloxamer/organic solvent mixture before such mixture has been dried. In other embodiments, the rapamycin composition can be formed by blending rapamycin with the preformed flowable powder excipient.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated

EXAMPLES

Example 1

Effects of Pluronics as Inhibitors of ABC Efflux Mechanisms

Confluent monolayers of MCF-7 ADR adriamycin resistant cells were washed, trypsinized with typsin-EDTA, and washed with PBS pH 7.2. The cells after washing were distributed into 5 ml polystyrene tubes, $5 \times 10^5$ cells (500 microliter) per tube. The tubes were centrifuged at 1200 RPM and PBS was decanted. The cells were then re-suspended in PBS containing 500 nM Rhodamine 123 and various concentrations of Pluronics, as listed in Table 1 below; reference samples with no Pluronic, and with 0.05% L61 were included in each tested series. All samples were prepared and tested in triplicates, and the presented results represent the average. Cells were incubated at 37° C. with 5% $CO_2$ for 45 minutes. After the incubation the samples were cooled to 4° C., centrifuged at 1200 RPM, washed once with 4 ml cold PBS, and re-suspended in 500 microliter cold PBS. Cells suspension, 300 microliter/well were transferred into 96-well polystyrene plates and the fluorescence was measured $\lambda_{Ex}$ 485 nm, and emission $\lambda_{Em}$ 530 nm. The increased fluorescence of the samples incubated with Pluronics vs. fluorescence of samples not containing Pluronics is interpreted as the enhancement of Rhodamine 123 uptake. This enhancement is normalized to the effect caused by 0.05% solution of Pluronic L61.

The above results demonstrate that multiple polymers of the structure POE-POP-POE cause enhancement of Rhodamine 123 uptake to MCF-7 ADR cells, interpreted as inhibition of ABC efflux mechanisms in these cells. The particularly effective Pluronics are L81, L92 and L61.

Example 2

Adhesiveness of Pluronic Mixtures

Mixtures of the below listed Pluronics were prepared employing either methanol or dichloromethane as a solvent using the following procedure. Precisely weighted amounts of Pluronics, as described in Table 2 below, were placed in graduated plastic vials. 5 mL of either anhydrous ethanol or dichloromethane were added to each vial, and the materials were mixed until homogenous. The mixtures were then placed in a SpeedVac system and the solvent removed under reduced pressure while centrifuging the samples to prevent spill. The residue materials were crushed with a glass rod to convert solids into powder. The material from each vial was subsequently transferred into another weighted container by tapping the capsized vial, and amount transferred was determined by weight. The material was presumed non-adhesive if at least 95% of the mass has been transferred. The results are listed in Table 2 below.

TABLE 2

| No. | Hydrophobic | [g] | Hydrophilic | [g] | Proportion (w/w) | Ethanol Adhesive | Dichloromethane Adhesive |
|---|---|---|---|---|---|---|---|
| 1 | L61 | 0.11 | F127 | 0.89 | 1:8 | No | No |
| 2 | L61 | 0.20 | F127 | 0.80 | 1:4 | No | No |
| A1 | L61 | 0.25 | F127 | 0.75 | 1:3 | Yes | Yes |
| A2 | L61 | 0.33 | F127 | 0.67 | 1:2 | Yes | Yes |
| 3 | L81 | 0.11 | F127 | 0.89 | 1:8 | No | No |
| 4 | L81 | 0.20 | F127 | 0.80 | 1:4 | No | No |
| B1 | L81 | 0.25 | F127 | 0.75 | 1:3 | Yes | Yes |
| B2 | L81 | 0.33 | F127 | 0.67 | 1:2 | Yes | Yes |
| 5 | L92 | 0.10 | F87 | 0.90 | 1:9 | No | No |
| 6 | L92 | 0.11 | F87 | 0.89 | 1:8 | No | No |
| 7 | L92 | 0.20 | F87 | 0.80 | 1:4 | No | No |
| C1 | L92 | 0.25 | F87 | 0.75 | 1:3 | Yes | Yes |

TABLE 1

Effect of Pluronics on uptake of Rhodamine 123 into MCF-7 ADR cells

| Pluronic name | Pluronic concentration [%] | | | | | | | Equivalent Conc.* | Potency** |
|---|---|---|---|---|---|---|---|---|---|
| | 0.0005 | 0.0015 | 0.005 | 0.015 | 0.05 | 0.15 | 0.5 | | |
| | Relative Rhodamine 123 uptake enhancement | | | | | | | | |
| L31 | 0.011 | 0.000 | 0.044 | 0.261 | 0.455 | 0.588 | 0.657 | 0.13% | 4 |
| L61 | 0.014 | 0.055 | 0.483 | 0.854 | 1.000 | 1.053 | | 0.007% | 70 |
| L62 | 0.047 | 0.007 | 0.088 | 0.602 | 1.183 | | | 0.014% | 35 |
| L64 | | 0.021 | 0.032 | 0.167 | 0.646 | 0.907 | | 0.04% | 11 |
| L81 | 0.055 | 0.253 | 0.938 | 1.228 | 1.091 | | | 0.003% | 162 |
| P84 | | 0.008 | 0.001 | 0.026 | 0.316 | 0.925 | | 0.09% | 6 |
| P85 | | 0.009 | 0.035 | 0.065 | 0.215 | 0.469 | 0.564 | 0.5% | 1 |
| L92 | 0.012 | 0.092 | 0.669 | 1.251 | | | | 0.004% | 115 |
| L101 | | 0.028 | 0.206 | 0.999 | 1.095 | | | 0.01% | 53 |
| P103 | | 0.039 | 0.137 | 0.292 | 1.367 | | | 0.024% | 21 |
| P104 | | 0.000 | 0.059 | 0.106 | 0.171 | 0.290 | 0.690 | 0.4% | 1 |
| L121 | | 0.039 | 0.079 | 0.260 | 0.849 | 0.947 | | 0.03% | 15 |
| P123 | | 0.000 | 0.010 | 0.053 | 0.634 | 1.115 | 1.141 | 0.05% | 11 |

*Equivalent concentration - concentration of the polymer of the potency equivalent to 0.5% Pluronic P85, determined from interpolation of experimental data
**Potency in Rhodamine 123 uptake enhancement, relative to 0.5% Pluronic P85

TABLE 2-continued

| No. | Hydro-phobic | [g] | Hydro-philic | [g] | Proportion (w/w) | Ethanol Adhesive | Dichloromethane Adhesive |
|---|---|---|---|---|---|---|---|
| C2 | L92 | 0.33 | F87 | 0.67 | 1:2 | Yes | Yes |
| 8 | L92 | 0.10 | F108 | 0.90 | 1:9 | No | No |
| 9 | L92 | 0.11 | F108 | 0.89 | 1:8 | No | No |
| 10 | L92 | 0.20 | F108 | 0.80 | 1:4 | No | No |
| D1 | L92 | 0.25 | F108 | 0.75 | 1:3 | No | Yes |
| D2 | L92 | 0.33 | F108 | 0.67 | 1:2 | Yes | Yes |
| 11 | L92 | 0.10 | F127 | 0.90 | 1:9 | No | No |
| 12 | L92 | 0.11 | F127 | 0.89 | 1:8 | No | No |
| 13 | L92 | 0.20 | F127 | 0.80 | 1:4 | No | No |
| 14 | L92 | 0.25 | F127 | 0.75 | 1:3 | No | No |
| E1 | L92 | 0.33 | F127 | 0.67 | 1:2 | Yes | Yes |

The above results demonstrate that the compositions of the present invention are flowable, non-adhesive powders.

Example 3

Compressibility of Pluronic Mixtures (as Indicated by Carr Index)

The bulk density ($\rho_B$), tap density ($\rho_T$) of each of the non-adhesive compositions produced above were measured, and the Can Index $C=100*(1-\rho_B/\rho_T)$ calculated. As a comparison, identical compositions were prepared employing water as the solvent, followed by freeze drying of the aqueous solution. The Can Indices of such compositions were similarly calculated. The results of such measurements are provided in Table 3 below.

TABLE 3

| No. | Hydro-phobic | [g] | Hydro-philic | [g] | Proportion (w/w) | Carr Index Ethanol | Carr Index Dichloromethane | Carr Index Water |
|---|---|---|---|---|---|---|---|---|
| 1 | L61 | 0.11 | F127 | 0.89 | 1:8 | 5.26 | 10.00 | 22.3 |
| 2 | L61 | 0.20 | F127 | 0.80 | 1:4 | 16.67 | 9.09 | 28.0 |
| 3 | L81 | 0.11 | F127 | 0.89 | 1:8 | 0.00 | 5.00 | 16.8 |
| 4 | L81 | 0.20 | F127 | 0.80 | 1:4 | 0.00 | 8.00 | 22.0 |
| 5 | L92 | 0.10 | F87 | 0.90 | 1:9 | 5.00 | 0.00 | 20.0 |
| 6 | L92 | 0.11 | F87 | 0.89 | 1:8 | 5.00 | 0.00 | 31.4 |
| 7 | L92 | 0.20 | F87 | 0.80 | 1:4 | 9.09 | 8.70 | 28.6 |
| 8 | L92 | 0.10 | F108 | 0.90 | 1:9 | 8.70 | 5.00 | 13.0 |
| 9 | L92 | 0.11 | F108 | 0.89 | 1:8 | 8.70 | 10.00 | 13.6 |
| 10 | L92 | 0.20 | F108 | 0.80 | 1:4 | 8.33 | 5.00 | 23.2 |
| 11 | L92 | 0.10 | F127 | 0.90 | 1:9 | 5.26 | 5.00 | 10.0 |
| 12 | L92 | 0.11 | F127 | 0.89 | 1:8 | 5.00 | 5.00 | 16.0 |
| 13 | L92 | 0.20 | F127 | 0.80 | 1:4 | 5.26 | 5.00 | 24.6 |
| 14 | L92 | 0.25 | F127 | 0.75 | 1:3 | 0.00 | 13.04 | 28.9 |

The above results show that the powders produced by the process of this invention exhibit unexpectedly lower Carr Indices, and are thus more compressible.

Example 4

Preparation of Rapamycin Composition 1 gram of rapamycin was dissolved in 25 ml of ethanol. After that the solution was mixed with 5 grams of L-92 dissolved in 200 ml of 20% F-127 solution of ethanol and water mixture (97/3V/V). The solution was incubated at 20-25° C. with constant stirring. The ethanol was removed using speed vac and the formulation further dried using high vacuum.

Formulation Composition:

| 40.0 g | F-127 |
|---|---|
| 5.0 g | L-92 |
| 1.0 g | Rapamycin |

Example 5

Preparation of a Rapamycin Composition with F-127, L-92 and Citric Acid 1 gram of rapamycin was dissolved in 25 ml of ethanol. After that the solution was mixed with 5 grams of L-92 and 2 grams of citric acid dissolved in 200 ml of 20% F-127 solution of ethanol and water mixture (97/3V/V). The solution was incubated at 20-25° C. for 30 minutes with constant stirring. The ethanol was removed using speed vac and further dried the formulation using high vacuum.

Formulation Composition:

| 40.0 g | F-127 |
|---|---|
| 5.0 g | L-92 |
| 1.0 g | Rapamycin |
| 2.0 g | Citric acid |

Example 6

Preparation of a Rapamycin Composition with F-127, L-92 and Citric Acid 1 gram of rapamycin was dissolved in 25 ml of ethanol. After that the solution was mixed with 5 grams of L-92 and 2 grams of citric acid dissolved in 200 ml of 20% F-127 solution of ethanol and water mixture (97/3V/V). The solution was incubated at 20-25° C. for 30 minutes with constant stirring. The ethanol was removed using speed vac and further dried the formulation using high vacuum. The solution was dissolved in distill water and freeze dried.

Formulation Composition:

| 40.0 g | F-127 |
|---|---|
| 5.0 g | L-92 |
| 1.0 g | Rapamycin |
| 2.0 g | Citric acid |

Example 7

Solubility and Stability of Formulation 23 mg of the solid formulations prepared according to Examples 4-6 were reconstituted by adding 1 ml of water. The solubility of all the sample were tested by mixing the samples on vortex. The samples after dissolving were inspected visually. The results are shown in Table 4.

TABLE 4

| | Observation of reconstructed solution (hours) | | | |
|---|---|---|---|---|
| Examples | 0 | 2 | 3 | 8 |
| 4 | Clear | Clear | Clear | Turbid |
| 5 | Clear | Clear | Clear | Clear |
| 6 | Clear | Clear | Clear | Clear |

The results indicate that the compressible rapamycin formulations of this invention will rapidly dissolve. It also demonstrates the stabilizing effect of the citric acid.

Example 8

Bioavailability of Rapamycin Formulations

Employing the process and ingredients described in Example 5 above, a quantity of a "polymeric rapamycin" was prepared. As a comparison, a "free rapamycin" composition comprising unformulated rapamycin was also prepared.
The polymeric rapamycin formulation was administered as a single dose (either orally or intravenously) to two groups of outbred female ICR mice. The free rapamycin was administered orally only to a third group.

Periodically, at the time points indicated in Table 5 below, blood samples were taken from 3 mice in each group. Whole blood was collected into EDTA-blood tubes, inverted a few times, and stored at 0° C. on ice in dark container during experiment. At the end of experiment all samples were placed at −70° C. for storage. Since rapamycin is light sensitive, the formulated drug and blood samples were protected from the light at all time during the experiment.

A pharmacokinetic analysis was performed using data from individual mice for which the mean and standard error of the mean (SEM) were calculated for each group using PK Solutions software (Version 2.0). The results of such analysis are summarized in Table 5 below:

TABLE 5

Concentration of Rapamycin in whole blood at Different Time Points

| Time (hr) | Polymeric Rapamycin IV, 0.4 mg/kg Conc (ng/ml) | Polymeric Rapamycin Oral 4 mg/kg Conc (ng/ml) | Free Rapamycin Oral 4 mg/kg Conc (ng/ml) |
| --- | --- | --- | --- |
| 0.04 | 958 | Not Measured | Not Measured |
| 0.25 | 532 | 656 | ND |
| 0.5 | 476 | 500 | ND |
| 1 | 316 | 400 | ND |
| 2 | 247 | 480 | ND |
| 4 | 217 | 200 | ND |
| 8 | 76 | 173 | ND |
| 16 | 50 | 11 | ND |
| 24 | 21 | 16 | ND |

ND—not detected

The above data indicates that the polymeric rapamycin formulation significantly enhances both the stability and bioavailability of rapamycin, permitting the oral administration of such drug.

What is claimed is:

1. A dry, flowable and compressible composition comprising:
   a. a hydrophobic poly(ethylene oxide)-polypropylene oxide)-poly(ethylene oxide) block copolymer;
   b. a hydrophilic poly(ethylene oxide)-polypropylene oxide)-poly(ethylene oxide) block copolymer; and
   c. rapamycin.

2. The composition of claim 1 wherein said composition comprises rapamycin and a mixture selected from the group consisting of:
   i. (a) a hydrophobic poly(ethylene oxide)-polypropylene oxide)-poly(ethylene oxide) block copolymer having an average molecular weight of about 2000 and a hydrophobe weight percentage of about 90% and (b) a hydrophilic poly(ethylene oxide)-poly(propylene oxide)-poly(ethylene oxide) block copolymer having an average molecular weight of about 12,600 and a hydrophobe weight percentage of about 30%, having a w/w proportion of a:b of about 1:4 or higher;
   ii. (a) a hydrophobic poly(ethylene oxide)-polypropylene oxide)-poly(ethylene oxide) block copolymer having an average molecular weight of about 2750 and a hydrophobe weight percentage of about 90% and (b) a hydrophilic poly(ethylene oxide)-polypropylene oxide)-poly(ethylene oxide) block copolymer having an average molecular weight of about 12,600 and a hydrophobe weight percentage of about 30%, having a w/w proportion of a:b of about 1:3 or higher;
   iii. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 7,700 and a hydrophobe weight percentage of about 30%, having a w/w proportion of a:b of about 1:4 or higher;
   iv. (a) a hydrophobic poly(ethylene oxide)-poly(propylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 14,600 and a hydrophobe weight percentage of about 20%, having a w/w proportion of a:b of about 1:3 or higher; and
   v. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 12,600 and a hydrophobe weight percentage of about 30%, having a w/w proportion of a:b of about 1:4 or higher.

3. The composition of claim 2 wherein such composition comprises:
   i. (a) a poly(ethylene oxide)-polypropylene oxide)-poly(ethylene oxide) block copolymer having an average molecular weight of about 3650 and a hydrophobe weight percentage of about 80% and (b) a poly(ethylene oxide)-polypropylene oxide)-poly(ethylene oxide) block copolymer having an average molecular weight of about 12,600 and a hydrophobe weight percentage of about 30%, having a w/w proportion of (a):(b) of about 1:4 or higher; and
   ii. rapamycin.

4. The composition of claim 1 wherein said composition comprises at least about 5% by weight of a hydrophilic poly(ethylene oxide)-poly(propylene oxide)-poly(ethylene oxide) block copolymer, based upon the total weight of the hydrophilic poly(ethylene oxide)-poly(propylene oxide)-poly(ethylene oxide) block copolymer plus the hydrophobic poly(ethylene oxide)-polypropylene oxide)-poly(ethylene oxide) block copolymer.

5. The composition of claim 4 wherein said composition comprises at least about 10% by weight of a hydrophilic poly(ethylene oxide)-poly(propylene oxide)-poly(ethylene oxide) block copolymer, based upon the total weight of the hydrophilic poly(ethylene oxide)-poly(propylene oxide)- poly(ethylene oxide) block copolymer plus the hydrophobic poly(ethylene oxide)-polypropylene oxide)-poly(ethylene oxide) block copolymer.

6. The composition of claim 1 wherein said composition has a Carr Index of less than about 20.

7. The composition of claim 6 wherein said composition has a Carr Index of less than about 10.

8. The composition of claim 7 wherein said composition has a Carr Index of less than about 5.

9. The composition of claim 1 which further comprises a stabilizer.

10. The composition of claim 9 wherein the stabilizer is citric acid.

11. A process for preparing a dry, flowable and compressible rapamycin composition comprising the steps of:
   a. mixing a (i) a hydrophobic poly(ethylene oxide)-polypropylene oxide)-poly(ethylene oxide) block copolymer; (ii) a hydrophilic poly(ethylene oxide)-polypropylene oxide)-poly(ethylene oxide) block copolymer; and (iii) rapamycin; in an organic solvent to form an organic mixture; and
   b. drying the organic mixture.

12. The process of claim 11 wherein the poly(ethylene oxide)-poly(propylene oxide)-poly(ethylene oxide) block copolymers are selected from the group consisting of:
   i. (a) a hydrophobic poly(ethylene oxide)-polypropylene oxide)-poly(ethylene oxide) block copolymer having an average molecular weight of about 2000 and a hydrophobe weight percentage of about 90% and (b) a hydrophilic poly(ethylene oxide)-polypropylene oxide)-poly(ethylene oxide) block copolymer having an average molecular weight of about 12,600 and a hydrophobe weight percentage of about 30%, having a w/w proportion of a:b of about 1:4 or higher;
   ii. (a) a hydrophobic poly(ethylene oxide)-polypropylene oxide)-poly(ethylene oxide) block copolymer having an average molecular weight of about 2750 and a hydrophobe weight percentage of about 90% and (b) a hydrophilic poly(ethylene oxide)-polypropylene oxide)-poly(ethylene oxide) block copolymer having an average molecular weight of about 12,600 and a hydrophobe weight percentage of about 30%, having a w/w proportion of a:b of about 1:3 or higher;
   iii. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 7,700 and a hydrophobe weight percentage of about 30%, having a w/w proportion of a:b of about 1:4 or higher;
   iv. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 14,600 and a hydrophobe weight percentage of about 20%, having a w/w proportion of a:b of about 1:3 or higher; and
   v. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-poly(ethylene oxide) block copolymer having an average molecular weight of about 12,600 and a hydrophobe weight percentage of about 30%, having a w/w proportion of a:b of about 1:4 or higher.

13. The process of claim 11 wherein the organic solvent is selected from the group consisting of alcohols and halogenated hydrocarbons.

14. The process of claim 11 wherein the organic solvent is ethanol.

15. The process of claim 11 wherein the organic solvent is dichloromethane.

16. The process of claim 11 wherein a minor amount of water is added to the organic solvent.

17. The process of claim 16 wherein the water comprises less than about 25% by weight of the organic solvent water mixture.

\* \* \* \* \*

UNITED STATES PATENT AND TRADEMARK OFFICE
CERTIFICATE OF CORRECTION

PATENT NO.       : 8,912,215 B2
APPLICATION NO.  : 13/324407
DATED            : December 16, 2014
INVENTOR(S)      : Pietrzynski et al.

Page 1 of 4

It is certified that error appears in the above-identified patent and that said Letters Patent is hereby corrected as shown below:

In the claims:

Column 11, lines 56-59, in claim 1:
"a. a hydrophobic poly(ethylene oxide)-polypropylene
    oxide)-poly(ethylene oxide) block copolymer;
b. a hydrophilic poly(ethylene oxide)-polypropylene
    oxide)-poly(ethylene oxide) block copolymer; and"
should read:
--a. a hydrophobic poly(ethylene oxide)-poly(propylene
    oxide)-poly(ethylene oxide) block copolymer;
b. a hydrophilic poly(ethylene oxide)-poly(propylene
    oxide)-poly(ethylene oxide) block copolymer; and--;

Column 11, lines 64-65, in claim 1:
"i. (a) a hydrophobic poly(ethylene oxide)-polypropylene
    oxide)-poly(ethylene oxide)"
should read:
--i. (a) a hydrophobic poly(ethylene oxide)-poly(propylene
    oxide)-poly(ethylene oxide)--;

Column 12, lines 6-10, in claim 2:
"ii. (a) a hydrophobic poly(ethylene oxide)-polypropylene
    oxide)-poly(ethylene oxide) block copolymer having an
    average molecular weight of about 2750 and a hydro-
    phobe weight percentage of about 90% and (b) a hydro-
    philic poly(ethylene oxide)-polypropylene oxide)-"
should read:
--ii. (a) a hydrophobic poly(ethylene oxide)-poly(propylene
    oxide)-poly(ethylene oxide) block copolymer having an Signed and Sealed this
Twenty-eighth Day of July, 2015

Michelle K. Lee
*Director of the United States Patent and Trademark Office* average molecular weight of about 2750 and a hydrophobe weight percentage of about 90% and (b) a hydrophilic poly(ethylene oxide)-poly(propylene oxide)- --;

Column 12, lines 15-19, in claim 2:
"iii. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-"
should read:
--iii. (a) a hydrophobic poly(ethylene oxide)-poly(propylene oxide)-poly(ethylene oxide) block copolymer having an average molecular weight of about 3650 and a hydrophobe weight percentage of about 80% and (b) a hydrophilic poly(ethylene oxide)-poly(propylene oxide)- --;

Column 12, lines 27-28, in claim 2:
"poly(ethylene oxide)-polypropylene oxide)-"
should read:
--poly(ethylene oxide)-poly(propylene oxide)- --;

Column 12, lines 33-37, in claim 2:
"v. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-"
should read:
--v. (a) a hydrophobic poly(ethylene oxide)-poly(propylene oxide)-poly(ethylene oxide) block copolymer having an average molecular weight of about 3650 and a hydrophobe weight percentage of about 80% and (b) a hydrophilic poly(ethylene oxide)-poly(propylene oxide)- --;

Column 12, lines 44-48, in claim 3:
"i. (a) a poly(ethylene oxide)-polypropylene oxide)-poly(ethylene oxide) block copolymer having an average molecular weight of about 3650 and a hydrophobe weight percentage of about 80% and (b) a poly(ethylene oxide)-polypropylene oxide)-poly(ethylene"
should read:
--i. (a) a poly(ethylene oxide)-poly(propylene oxide)-poly(ethylene oxide) block copolymer having an average molecular weight of about 3650 and a hydrophobe

CERTIFICATE OF CORRECTION (continued)
U.S. Pat. No. 8,912,215 B2 weight percentage of about 80% and (b) a poly(ethylene oxide)-poly(propylene oxide)-poly(ethylene--;

Column 12, lines 60-61, in claim 4:
"oxide)-polypropylene oxide)-poly(ethylene oxide) block copolymer."
should read:
--oxide)-poly(propylene oxide)-poly(ethylene oxide) block copolymer.--;

Column 13, lines 2-3, in claim 5:
"oxide)-polypropylene oxide)-poly(ethylene oxide) block copolymer."
should read:
--oxide)-poly(propylene oxide)-poly(ethylene oxide) block copolymer.--;

Column 13, lines 16-19, in claim 11:
"a. mixing a (i) a hydrophobic poly(ethylene oxide)-polypropylene oxide)-poly(ethylene oxide) block copolymer; (ii) a hydrophilic poly(ethylene oxide)-polypropylene oxide)-"
should read:
--a. mixing a (i) a hydrophobic poly(ethylene oxide)-poly(propylene oxide)-poly(ethylene oxide) block copolymer; (ii) a hydrophilic poly(ethylene oxide)-poly(propylene oxide)- --;

Column 13, lines 26-30, in claim 12:
"i. (a) a hydrophobic poly(ethylene oxide)-polypropylene oxide)-poly(ethylene oxide) block copolymer having an average molecular weight of about 2000 and a hydrophobe weight percentage of about 90% and (b) a hydrophilic poly(ethylene oxide)-polypropylene oxide)-"
should read:
--i. (a) a hydrophobic polyethylene oxide)-poly(propylene oxide)-poly(ethylene oxide) block copolymer having an average molecular weight of about 2000 and a hydrophobe weight percentage of about 90% and (b) a hydrophilic poly(ethylene oxide)-poly(propylene oxide)- --;

Column 13, lines 35-39, in claim 12:
"ii. (a) a hydrophobic poly(ethylene oxide)-polypropylene oxide)-poly(ethylene oxide) block copolymer having an average molecular weight of about 2750 and a hydrophobe weight percentage of about 90% and (b) a hydrophilic poly(ethylene oxide)-polypropylene oxide)-"
should read:

CERTIFICATE OF CORRECTION (continued)
U.S. Pat. No. 8,912,215 B2

--ii. (a) a hydrophobic poly(ethylene oxide)-poly(propylene oxide)-poly(ethylene oxide) block copolymer having an average molecular weight of about 2750 and a hydrophobe weight percentage of about 90% and (b) a hydrophilic poly(ethylene oxide)-poly(propylene oxide)- --;

Column 14, lines 3-7, in claim 12:
"iii. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-"
should read:
--iii. (a) a hydrophobic poly(ethylene oxide)-poly(propylene oxide)-poly(ethylene oxide) block copolymer having an average molecular weight of about 3650 and a hydrophobe weight percentage of about 80% and (b) a hydrophilic poly(ethylene oxide)-poly(propylene oxide)- --;

Column 14, lines 12-16, in claim 12:
"iv. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-"
should read:
--iv. (a) a hydrophobic poly(ethylene oxide)-poly(propylene oxide)-poly(ethylene oxide) block copolymer having an average molecular weight of about 3650 and a hydrophobe weight percentage of about 80% and (b) a hydrophilic poly(ethylene oxide)-poly(propylene oxide)- --; and Column 14, lines 21-25, in claim 12:
"v. (a) a hydrophobic poly(ethylene oxide)-polypropylene oxide)-poly(ethylene oxide) block copolymer having an average molecular weight of about 3650 and a hydrophobe weight percentage of about 80% and (b) a hydrophilic poly(ethylene oxide)-polypropylene oxide)-"
should read:
--v. (a) a hydrophobic poly(ethylene oxide)-poly(propylene oxide)-poly(ethylene oxide) block copolymer having an average molecular weight of about 3650 and a hydrophobe weight percentage of about 80% and (b) a hydrophilic polyethylene oxide)-poly(propylene oxide)- --.